United States Patent [19]

Kondo et al.

[11] 4,323,700

[45] Apr. 6, 1982

[54] PROCESS FOR PREPARING BENZOPHENONE DERIVATIVES

[75] Inventors: Mitsuru Kondo; Hiroshi Iwasaki, both of Kawanishi; Kiyoshi Yasui, Mukomotomachi; Makoto Miyake, Nishinomiya, all of Japan

[73] Assignee: Kanzaki Paper Manufacturing Co., Ltd., Hyogo, Japan

[21] Appl. No.: 73,108

[22] Filed: Sep. 6, 1979

Related U.S. Application Data

[63] Continuation of Ser. No. 772,124, Feb. 25, 1977, abandoned.

[30] Foreign Application Priority Data

Mar. 4, 1976 [JP]   Japan .................................. 51-23912

[51] Int. Cl.³ ............................................ C07C 59/76
[52] U.S. Cl. .................................. 562/460; 562/418; 562/419; 562/420; 562/468; 260/326.47; 544/172; 544/242; 544/335; 546/98

[58] Field of Search ............... 562/460, 418, 419, 420, 562/468; 544/172, 242, 335; 260/326.47; 546/98

[56] References Cited

U.S. PATENT DOCUMENTS

2,753,373  7/1955  Hutchings et al. ................. 260/521
3,634,500  1/1972  McCormick et al. .............. 260/517
4,057,573 11/1977  Haas et al. ............................. 560/8

FOREIGN PATENT DOCUMENTS

937378  9/1963  United Kingdom ................ 562/459

OTHER PUBLICATIONS

Grabe et al., Berichte 21, pp. 2003-2005, (1888).

*Primary Examiner*—Paul J. Killos
*Attorney, Agent, or Firm*—Morgan, Finnegan, Pine, Foley & Lee

[57] ABSTRACT

A process is described for preparing benzophenone derivatives of a high purity in an extremely high yield from 3-phenylphthalide derivatives with the use of at least one oxidizing agent.

17 Claims, No Drawings

PROCESS FOR PREPARING BENZOPHENONE DERIVATIVES

This is a continuation of application Ser. No. 772,124 filed Feb. 25, 1977, now abandoned.

BACKGROUND OF THE INVENTION

This invention relates to a novel process for preparing benzophenone derivatives. Particularly, this invention relates to a novel process for preparing benzophenone derivatives useful as an intermediate in the preparation of anthraquinone dyes and colourless chromogenic compounds which form coloured markings upon contact with acidic materials by electron donor-acceptor colour-forming reaction. More particularly, this invention relates to a novel process for preparing benzophenone derivatives represented by the following general formula (I):

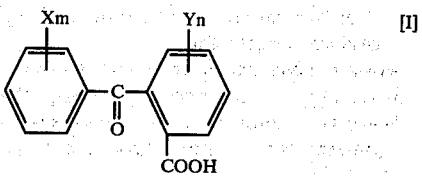

wherein each of X and Y is hydrogen, halogen, nitro group, alkyl group, substituted alkyl group, amino group, substituted amino group, hydroxyl group, or substituted hydroxyl group; each of m and n is an integer of from 1 to 4.

There are known methods for preparing benzophenone derivatives represented by the general formula (I), for example U.S. Pat. No. 3,540,912 discloses a method in which the benzophenone derivatives are prepared by reacting aniline derivatives with substituted phthalic anhydrides in benzene with the use of Friedel-Crafts type catalysts. However, Friedel-Crafts reaction is prevented with the presence of water, because the catalysts are decomposed by water. Accordingly, it should be careful to handle the catalysts and it is necessary to use a dehydrated solvent and a complicated reactor which is completely protected from moisture. Additionally, since a large amount of isomers is produced because of the use of substituted phthalic acids, isolation is required to obtain the desired final product. This will result in reducing the yield of product.

An object of the invention is to provide a novel process for preparing benzophenone derivatives of a high purity in an extremely high yield.

Other objects and advantages of the invention will become apparent from the following description.

SUMMARY OF THE INVENTION

According to the invention, benzophenone derivatives represented by the general formula (I) are prepared by making 3-phenylphthalide derivatives represented by the following general formula (II) disperse or dissolve into an aqueous solution of alkali salt and then oxidize with the use of at least one oxidizing agent:

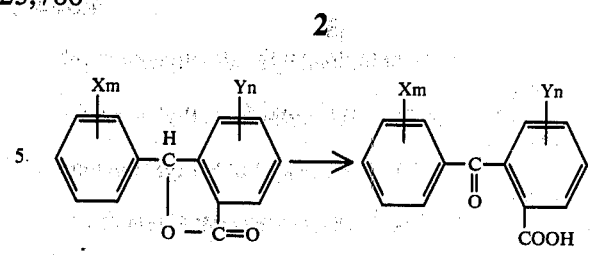

wherein X, Y, m and n are the same as described above.

DETAILED DESCRIPTION OF THE INVENTION 3-phenylphthalide derivative represented by the above described general formula (II) which is used in this invention is prepared, as shown as follows, from benzene derivative (III) and o-phthalaldehydic acid derivative (IV) by dehydration condensation, or from benzaldehyde derivative (V) and benzoic acid derivative (VI) by dehydration condensation:

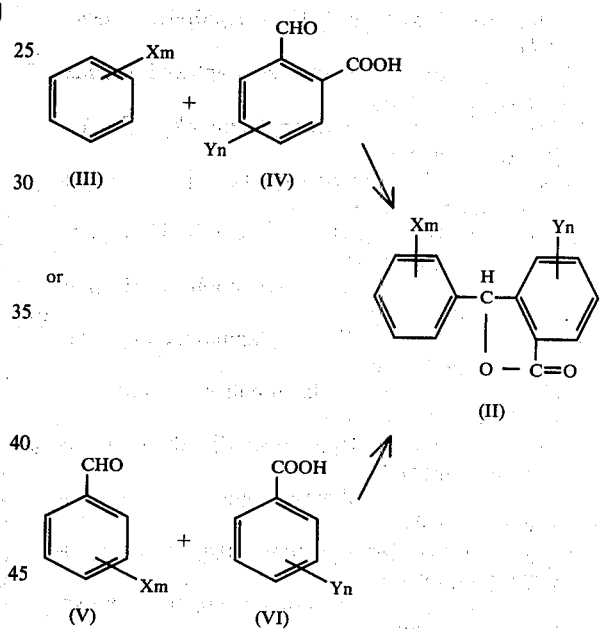

wherein X, Y, m and n are the same as described above.

As the typical compounds of 3-phenylphthalide derivatives represented by the above general formula (II) which are used in this invention, the following compounds may be exemplified;

3-(4-dimethylaminophenyl)phthalide,
3-(4-dimethylamino-2-methylphenyl)phthalide,
3-(4-dimethylamino-2-methoxyphenyl)phthalide,
3-(4-dimethylamino-2-methylthiophenyl)phthalide,
3-(4-dimethylamino-2-chlorophenyl)phthalide,
3-(4-dimethylamino-2-diethylaminophenyl)phthalide,
3-(4-diethylaminophenyl)phthalide,
3-(4-diethylamino-2-chlorophenyl)phthalide,
3-(4-diethylamino-2-methoxyphenyl)phthalide,
3-[4-(N-ethyl-N-benzyl)aminophenyl]phthalide,
3-[4-(N-methyl-N-P-tolyl)aminophenyl]phthalide,
3-(4-pyrrolidinophenyl)phthalide,
4-(julolidine-6-yl)phthalide,
3-phenyl-6-dimethylaminophthalide,
3-phenyl-6-diethylaminophthalide, 3-[2(or 3, or 4)-methylphenyl]-6-dimethylaminophthalide,
3-[2(or 3, or 4)-methoxyphenyl]-6-dimethylaminophthalide,
3-[2(or 3, or 4]-methoxyphenyl]-6-diethylaminophthalide,
3-[2-(or 3, or 4)-chlorophenyl]-6-dimethylaminophthalide,
3-[2-(or 3, or 4)-nitrophenyl]-6-dimethylaminophthalide,
3-[2-(or 3, or 4)-nitrophenyl]-6-diethylaminophthalide,
3-[2, 3(or 2, 4)-dimethylphenyl]-6-dimethylaminophthalide,
3-[2, 3(or 2, 4)-dimethoxyphenyl]-6-dimethylaminophthalide,
3-[2, 3(or 2, 4)-dimethoxyphenyl]-6-diethylaminophthalide,
3-[2, 3(or 2, 4)-dichlorophenyl]-6-dimethylaminophthalide,
3-(2-methyl-4-methoxyphenyl)-6-dimethylaminophthalide,
3-(2-methoxy-4-methylphenyl)-6-dimethylaminophthalide,
3-[2(or 3, or 4)-dimethylaminophenyl]-6-dimethylaminophthalide,
3-[2(or 3, or 4)-dimethylaminophenyl]-6-diethylaminophthalide,
3-[2(or 3, or 4)-dimethylaminophenyl]-6-N-methyl-N-P-tolylaminophthalide,
3-[2(or 3, or 4)-dimethylaminophenyl]-6-N-ethyl-N-benzylaminophthalide,
3[(2(or 3, or 4))-diethylaminophenyl]-6-dimethylaminophthalide,
3-[2(or 3, or 4)-diethylaminophenyl]-6-diethylaminophthalide,
3-[2(or 3, or 4)-dimethylaminophenyl]-5-chloro-6-dimethylaminophthalide,
3-[2(or 3, or 4)-dimethylaminophenyl]-5-chloro-6-diethylaminophthalide,
3-[2(or 3, or 4)-dimethylaminophenyl]-6-diallylaminophthalide,
3-[2(or 3, or 4)-dimethylaminophenyl]-6-dipropargylamino-phthalide,
3-[2(or 3, or 4)-dimethylaminophenyl]-6-pyrolidinophthalide,
3-[2(or 3, or 4)-dimethylaminophenyl]-6-pyrimidinophthalide,
3-[2(or 3, or 4)-dimethylaminophenyl]-6-morpholinophthalide,
3-(4-pyrrolidinophenyl)-6-dimethylaminophthalide,
3-(4-pyrimidinophenyl)-6-dimethylaminophthalide,
3-(julolidine-6-yl)-6-dimethylaminophthalide,
3-(4-morpholinophenyl)-6-dimethylaminophthalide,
3-[4-(N-methyl-N-benzyl)aminophenyl]-6-dimethylaminophthalide,
3-[4-(N-methyl-N-benzyl)aminophenyl]-6-diethylaminophthalide,
3-[4-(N-ethyl-N-benzyl)aminophenyl]-6-dimethylaminophthalide,
3-[4-(N-methyl-N-para-tolyl)aminophenyl]-6-dimethylamino-phthalide,
3-[4-(N-ethyl-N-para-tolyl)aminophenyl]-6-dimethylaminophthalide,
3-[4-(N-ethyl-N-para-tolyl)aminophenyl]-6-diethylaminophthalide,
3-(4-diallylaminophenyl)-6-dimethylaminophthalide,
3-(4-dipropargylaminophenyl)-6-dimethylaminophthalide,
3-(4-dimethylamino-2-methylphenyl)-6-dimethylaminophthalide,
3-(4-diethylamino-2-methylphenyl)-6-dimethylaminophthalide,
3-(4-dimethylamino-2-chlorophenyl)-6-dimethylaminophthalide,
3-(4-diethylamino-2-chlorophenyl)-6-dimethylaminophthalide,
3-(4-dimethylamino-2-methoxyphenyl)-6-dimethylaminophthalide,
3-(4-diethylamino-2-methoxyphenyl)-6-dimethylaminophthalide,
3-(4-dimethylamino-2-methylthiophenyl)-6-dimethylaminophthalide,
3-(4-diethylamino-2-methylphenyl)-5-chloro-6-dimethylaminophthalide,
3-(4-diethylamino-2-methylphenyl)-5-chloro-6-diethylaminophthalide,
3-(4-diethylamino-2-methoxyphenyl)-5-chloro-6-dimethylaminophthalide,
3-(4-diethylamino-2-methoxyphenyl)-5-chloro-6-diethylaminophthalide,
3-(4-dimethylaminophenyl)-6-methoxyphthalide,
3-(4-diethylaminophenyl)-6-ethoxyphthalide,
3-(4-diethylaminophenyl)-6-methoxyphthalide, and
3-(4-diethylamino-2-methoxyphenyl)-6-methoxyphthalide.

Among the above mentioned 3-phenylphthalide derivatives, those having Y at the 6 position are preferably used and preferably Y is an substituted amino group.

In the practice of the invention, 3-phenylphthalide derivatives are made to disperse or dissolve into an aqueous solution of alkali salt and oxidize with the use of at least one oxidizing agent at a temperature of 0° to 200° C. for the period between several minutes and several decades of hours to obtain benzophenone derivatives.

Among the alkali salts used in this invention, there may be included hydroxides and carbonates of alkali metals such as lithium, sodium and potassium, and alkaline earth metals such as calcium and magnesium. Hydroxides of alkali metals are preferably used, particularly sodium hydroxide and potassium hydroxide are most preferable.

Referring to the amount of such alkali salts, it may be controlled properly according to the kinds of 3-phenylphthalide derivatives and alkali salts, but it is preferable to use them in amounts equimolar with respect to 3-phenylphthalide derivatives or more.

Hydrophilic solvents such as methyl alcohol, ethyl alcohol, propyl alcohol and the like may be added to the aqueous solution of alkali salt, if necessary.

As an oxidizing agent, manganese compounds such as permanganates, manganates, manganese dioxide, manganese (III) salts and manganese acetate; chromic acid compounds such as chromic anhydride, chromic acid, perchromates, alkyl esters of chromic acid and chromyl chloride; lead compounds such as PbO, $PbO_2$ and $Pb(OCOCH_3)_4$; copper compounds such as CuO, $Cu(OH)_2$, $CuSO_4$, $Cu(OCOCH_3)_2$, $CuCl_2$ and $CuBr_2$; cobalt compounds such as $Co_2(SO_4)_3$ and $Co_3O_4$; cerium compounds such as $CeO_2$, $Ce(SO_4)_2$ and $Ce(SO_4)_3$; bismuth compounds such as $NaBiO_3$, BiO and $Bi(OCOCH_3)_2$; silver compounds such as $Ag_2O$, $AgOCOCH_3$ and $AgNO_3$; iron compounds such as $FeCl_3$, $Fe_2(SO_4)_3$ and potassium ferricyanate; $SeO_2$; $RuO_4$; $OsO_4$; inorganic peroxide such as hydrogen peroxide, Fenton's reagent, persulfuric acid and salts thereof; organic peroxides such as performic acid, peracetic acid, perpropionic acid, perbutyric acid, perbenzoic acid, monoperphthalic acid, monoperterephthalic acid, monopersuccinic acid and trifluoroperacetic acid; organic nitro compounds such as 2-nitropropane, nitrocyclohexane, nitrobenzene, nitroxylene, nitroanisole and nitrobenzene sulfonates; halides such as hypochlorites, chlorates, hypobromites and bromates; oxygen; ozone; ultraviolet ray; sulfoxides and chloranil are preferably used.

Among these oxidizing agents, organic nitro compounds are preferably used because of handling them easily and giving the product in high yields. Particularly nitrobenzene sulfonates superior in water solubility are most preferable. The reaction system may include not only one kind of these oxidizing agents but also two or more kinds of them.

The amount of oxidizing agents may be controlled according to the kinds of oxidizing agent to be used, but it may be usually used in an excess of a stoichiometric amount based on the amount of said 3-phenylphthalide derivatives having the general formula (II).

The process of the invention gives benzophenone derivatives at high purities and in extremely high yields, because the reaction is controlled very easily and the by-products are not formed appreciably.

Benzophenone derivatives obtained by the invention are very useful as an intermediate for preparing anthraquinone dyes and colorless chromogenic compounds which form coloured markings upon contact with acidic materials by electron donor-acceptor colour-forming reaction.

Accordingly, numeral novel colourless chromogenic compounds and anthraquinone dyes which have not been obtained by conventional methods in addition to well known compounds can be easily produced according to the invention. For example, benzophenone derivatives obtained by the invention are condensated with aniline derivatives or indole derivatives to produce various known or novel triarylmethane derivatives and fluoran derivatives. These compounds can be utilized for the production of pressure sensitive copying sheet which is disclosed in U.S. Pat. Nos. 2,730,456 and 2,730,457 and Japanese Pat. No. 511,757, heat sensitive copying sheet which is disclosed in U.S. Pat. Nos. 3,451,338 and 3,539,375 hectographic copying sheet, electron beam sensitive recording sheet, photosensitive sheet, electrographic heat sensitive recording sheet, ultrasonic recording sheet, toner for Xerox type copying sheet, and leuco ink.

There are shown in the following Table 1 several instances of triarylmethane derivatives and fluoran derivatives obtained by condensation of benzophenone derivatives produced according to the invention with aniline derivatives or indole derivatives. In Table 1, benzophenone derivatives obtained by the invention are given in the column A, aniline derivatives and indole derivatives are given in the column B, triarylmethane derivatives or fluoran derivatives produced by the reaction of the compound in the column A with the compound in the column B are given in the column C, the melting point of the triarylmethane derivatives or fluoran derivatives is given in the column D and the colours which are formed on contact with silica gel are shown in the column E.

TABLE 1

| A | B | C | D | E |
|---|---|---|---|---|
| [structure] | [structure] | [structure] | 180° C. | bluish violet |
| [structure] | [structure] | [structure] | 212–214° C. | blue |

TABLE 1-continued

| A | B | C | D | E |
|---|---|---|---|---|
| (structure) | (structure) | (structure) | 84–87° C. | bluish violet |
| (structure) | (structure) | (structure) | 90–93° C. | bluish violet |
| (structure) | (structure) | (structure) | 147–149° C. | bluish violet |
| (structure) | (structure) | (structure) | 143–145° C. | bluish violet |
| (structure) | (structure) | (structure) | 187–189° C. | bluish violet |

TABLE 1-continued

| A | B | C | D | E |
|---|---|---|---|---|
| 2-(dimethylamino)benzoyl-5-(dimethylamino)benzoic acid structure | N,N-dimethylaniline | lactone product structure | 220–223° C. | bluish violet |
| 3-(N-ethyl-N-ethylamino)benzoyl-4-(dimethylamino)benzoic acid structure | N,N-dimethylaniline | lactone product structure | 177–178° C. | bluish green |
| 2-methoxybenzoyl-4-(dimethylamino)benzoic acid structure | N,N-dimethylaniline | lactone product structure | 208–210° C. | green |
| 4-(dimethylamino)benzoyl-4-ethoxybenzoic acid structure | N,N-dimethylaniline | lactone product structure | 167–168° C. | green |
| 4-methoxybenzoyl-4-(dimethylamino)benzoic acid structure | 2-methylindole | lactone product structure | 147.5° C. | reddish violet |

TABLE 1-continued

| A | B | C | D | E |
|---|---|---|---|---|
| (3,4-dimethoxybenzoyl)-4-dimethylamino-benzoic acid | 2-methylindole | corresponding phthalide | 244° C. | reddish violet |
| (2,4-dimethoxybenzoyl)-dimethylamino-benzoic acid | 2-methylindole | corresponding phthalide | 213–215° C. | reddish violet |
| (4-methylbenzoyl)-dimethylamino-benzoic acid | 2-methylindole | corresponding phthalide | 134–135° C. | reddish violet |
| (2-methoxybenzoyl)-dimethylamino-benzoic acid | 3-hydroxy-N,N-dimethylaniline | corresponding xanthene | 197–199° C. | reddish brown |
| (2-methoxybenzoyl)-dimethylamino-benzoic acid | 3-hydroxy-N,N-diethylaniline | corresponding xanthene | 178–180° C. | reddish brown |

TABLE 1-continued

| A | B | C | D | E |
|---|---|---|---|---|
| 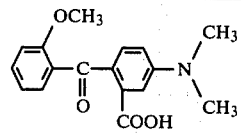 | 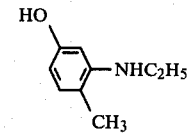 | 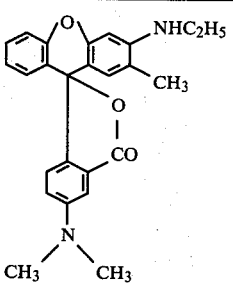 | 214–215° C. | reddish brown |

PREFERRED EMBODIMENT OF THE INVENTION

The following examples serve to illustrate the invention in more detail although the invention is not limited to the examples.

EXAMPLE 1

5 g of 3-(p-dimethylaminophenyl)-6-dimethylaminophthalide was dispersed in 20 cc of 10% aqueous solution of sodium hydroxide and the resultant mixture was heated at 90° C. for one hour with stirring to obtain a homogeneous solution. Then, 5 g of sodium m-nitrobenzenesulfonate was added to the solution, and the mixture was refluxed for 15 hours on an oil bath. After cooling pH of the solution was adjusted to 4.0 with an aqueous solution of acetic acid to precipitate yellow solid. The solid was filtrated and dissolved in aqueous solution of sodium carbonate. The insoluble material was removed by filtration and the pH of the filtrate was adjusted to 6.0 with acetic acid to precipitate yellow solid. This solid was filtered and then dried. The yield was 4.7 g. Recrystallization from ethanol gave yellow crystals having a melting point (hereinafter referred to as m.p.) of 269°–270° C. This compound is benzophenone derivative represented by the following formula:

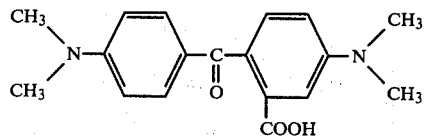

EXAMPLE 2

5 g of 3-(p-dimethylaminophenyl)-phthalide was dispersed into 20 cc of 10% aqueous solution of sodium hydroxide and the resultant mixture was heated at 90° C. for one hour with stirring to obtain a homogeneous solution. After cooling the solution to room temperature, 50 cc of 6% aqueous solution of potassium permanganate was dropped into the solution for about one hour. Then the solution was heated at 60° C. for one hour with stirring and cooled to precipitate manganese dioxide. The manganese dioxide was filtered off. Hydrochloric acid was added into the filtrate until the pH of the filtrate became 6.0 to precipitate pale yellow solid. The solid was filtered and then dried. The yield was 1.4 g. Recrystallization from a diluted aqueous solution of acetic acid gave benzophenone derivative represented by the following formula in the form of pale yellow crystals whose m.p. was 203° C.

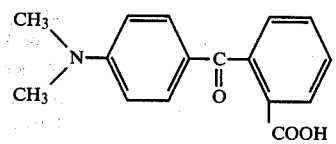

EXAMPLE 3

5 g of 3-p-(N-benzyl-N-ethyl)aminophenyl-phthalide and 5 cc of 30% aqueous solution of potassium hydroxide were mixed into 30 cc of nitrobenzene. The mixture was heated at 120° C. for 20 hours with stirring. Then the excess amount of nitrobenzene was removed by steam-distillation. The pH of the resultant solution was adjusted to 6.0 to precipitate brown solid. The solid was filtered and dried. The yield was 3.4 g. Recrystallization from methanol gave benzophenone derivative represented by the following formula in the form of pale yellow crystals whose m.p. was 177°–178° C.

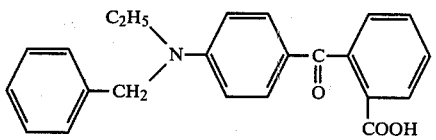

EXAMPLE 4

Example 1 was repeated except that 5 g of 3-(o-methoxyphenyl)-6-dimethylaminophthalide was used instead of 5 g of 3-(p-dimethylaminophenyl)-6-dimethylaminophthalide and the recrystallization was carried out from methanol instead of ethanol to obtain benzophenone derivative represented by the following formula in the form of pale yellow crystals whose m.p. was 213°–215° C. The yield was 3.8 g.

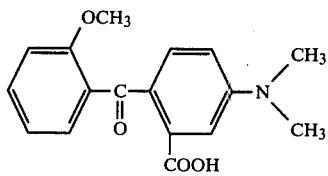

EXAMPLE 5

Example 1 was repeated except that 5 g of 3-(p-methoxyphenyl)-6-dimethylaminophthalide was used instead of 5 g of 3-(p-dimethylaminophenyl)-6-dimethylaminophthalide and the recrystallization was carried out from methanol instead of ethanol to obtain benzophenone derivative represented by the following formula in the form of pale yellow crystals whose m.p. was 228°–229° C. The yield was 4.4 g.

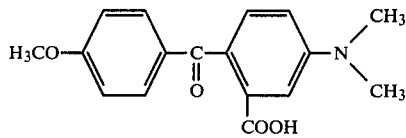

EXAMPLE 6

Example 5 was repeated except that 3-(p-methylphenyl)-6-dimethylaminophthalide was used instead of 3-(p-methoxyphenyl)-6-dimethylaminophthalide to obtain benzophenone derivative represented by the following formula in the form of pale yellow crystals whose m.p. was 221°–222° C. The yield was 4.7 g.

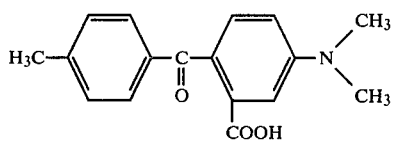

EXAMPLE 7

Example 5 was repeated except that 3-(3,4-dimethoxyphenyl)-6-dimethylaminophthalide was used instead of 3-(p-methoxyphenyl)-6-dimethylaminophthalide to obtain benzophenone derivative represented by the following formula in the form of pale yellow crystals whose m.p. was 238°–240° C. The yield was 3.5 g.

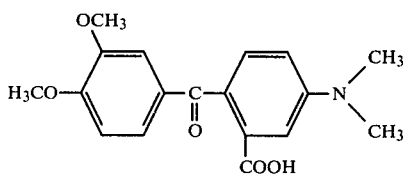

EXAMPLE 8

5 g of 3-(2-methyl-4-N,N-dimethylamino-phenyl)-phthalide was dispersed into 25 cc of 10% aqueous solution of sodium hydroxide and the resultant mixture was heated at 90° C. to form a homogeneous solution. After cooling the solution to 50° C., 35 cc of 15% aqueous solution of sodium persulfate was dropped into the solution for about 30 minutes with stirring. Further the solution was maintained at 50° C. for about 2 hours with stirring. After the termination of reaction, the pH of the solution was adjusted at 4 with aqueous solution of acetic acid to precipitate brown solid. The solid was filtrated and dissolved into aqueous solution of sodium carbonate. The insoluble material was removed by filtration and the filtrate was neutralized with an aqueous solution of acetic acid to precipitate yellowish brown solid. The solid was recrystallized from methanol to obtain benzophenone derivative represented by the following formula in the form of pale yellow crystals whose m.p. was 110° C. The yield was 1.9 g.

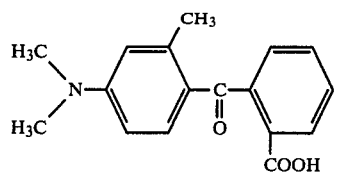

EXAMPLE 9

5 g of 3-(4-N-methyl-N-ethylamino-phenyl)-phthalide was dispersed into 25 cc of 10% aqueous solution of sodium hydroxide and the mixture was heated at 90° C. to form a homogeneous solution. The solution was cooled to room temperature and then 50 cc of 10% aqueous solution of ferric chloride was added dropwise into the solution for about 30 minutes with stirring. Further the solution was stirred for 5 hours to precipitate a solid. The solid was removed by filtration and the filtrate was neutralized with aqueous solution of acetic acid to precipitate brown solid. The solid was dissolved into aqueous solution of sodium carbonate. The insoluble material was removed by filtration and the filtrate was neutralized to obtain yellow precipitation. Recrystallization from methanol gave benzophenone derivative represented by the following formula in the form of pale yellowish green crystals whose m.p. was 175°–177° C. The yield was 1.3 g.

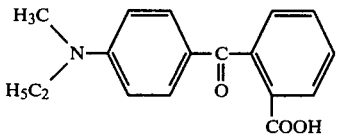

What we claim is:

1. A process for preparing benzophenone derivatives having the general formula

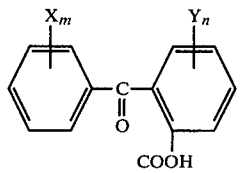

wherein each of X and Y is a substituent selected from the group consisting of a halogen; a nitro group; an alkyl group; an amino group substituted with two substituents selected from the group consisting of a saturated $C_{1-4}$ alkyl group, an allyl group, a propargyl group, a phenyl group, a tolyl group and a benzyl group; a morpholino group; a pyrimidino group; a pyrrolidino group; and a $C_{1-2}$ alkoxy group, each of m and n is 0 or an integer from 1 to 2, or XM

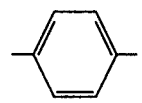

is a moiety selected from the group consisting of a juloidine moiety or a 1-butyl, 1,2,3,4-tetrahydroquinoline moiety which comprises dissolving a 3-phenylphthalide derivative having the general formula

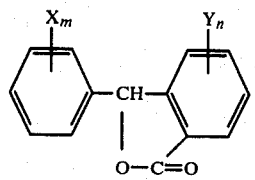

wherein X, Y, m and n are the same as described hereinbefore, into an aqueous solution of alkali salt and oxidizing said dispersed 3-phenylphthalide derivative with at least one oxidizing agent, said alkali salt being in at least an equimolar amount with respect to said 3-phenylphthalide derivative.

2. A process for preparing benzophenone derivative as defined in claim 1, wherein said 3-phenylphthalide derivative having the general formula (II) has Y at the 6 position.

3. A process for preparing a benzophenone derivative as defined in claim 2, wherein said Y is an amino group substituted with two substituents selected from the group consisting of a saturated $C_{1-4}$ alkyl group, an allyl group, a propargyl group, a phenyl group, a tolyl group and a benzyl group; a morpholino group; a pyrimido group or a pyrrolidino group.

4. A process for preparing benzophenone derivative as defined in claim 1, wherein said oxidizing agent is an organic nitro compound.

5. A process for preparing benzophenone derivative as defined in claim 4, wherein said organic nitro compound is nitrobenzenesulfonate.

6. A process for preparing benzophenone derivative as defined in claim 1, wherein said alkali salt is selected from hydroxides of alkali metal.

7. A process for preparing benzophenone derivative as defined in claim 6, wherein said hydroxide of alkali metal is sodium hydroxide or potassium hydroxide.

8. A process for preparing benzophenone derivative as defined in claim 1, wherein the oxidative reaction of said 3-phenylphthalide derivative is carried out at a temperature within the range of 0° to 200° C.

9. A process for preparing benzophenone derivatives as defined in claim 1, wherein said 3-phenylphthalide derivative is 3-(p-dimethylaminophenyl)-6-dimethylaminophthalide.

10. A process for preparing benzophenone derivatives as defined in claim 1, wherein said 3-phenylphthalide derivative is 3-(p-dimethylaminophenyl)-phthalide.

11. A process for preparing benzophenone derivatives as defined in claim 1, wherein said 3-phenylphthalide derivative is 3-p-(N-benzyl-N-ethyl)aminophenylphthalide.

12. A process for preparing benzophenone derivatives as defined in claim 1, wherein said 3-phenylphthalide derivative is 3-(o-methoxyphenyl)-6-dimethylaminophthalide.

13. A process for preparing benzophenone derivatives as defined in claim 1, wherein said 3-phenylphthalide derivative is 3-(p-methoxyphenyl)-6-dimethylaminophthalide.

14. A process for preparing benzophenone derivatives as defined in claim 1, wherein said 3-phenylphthalide derivative is 3-(p-methylphenyl)-6-dimethylaminophthalide.

15. A process for preparing benzophenone derivatives as defined in claim 1, wherein said 3-phenylphthalide derivative is 3-(3,4-dimethoxyphenyl)-6-dimethylaminophthalide.

16. A process for preparing benzophenone derivatives as defined in claim 1, wherein said 3-phenylphthalide derivative is 3-(2-methyl-4-N,N-dimethylaminophenyl)-phthalide.

17. A process for preparing benzophenone derivatives as defined in claim 1, wherein said 3-phenylphthalide derivative is 3-(4-N-methyl-N-ethylamino-phenyl)-phthalide.

* * * * *